United States Patent [19]

Busch, Jr.

[11] Patent Number: 5,478,551

[45] Date of Patent: Dec. 26, 1995

[54] NON-AQUEOUS COMPOSITION FOR HARDENING AND STRENGTHENING FINGERNAILS AND TOENAILS

[75] Inventor: Francis W. Busch, Jr., Southbury, Conn.

[73] Assignee: Prostrong Inc., Waterbury, Conn.

[21] Appl. No.: 258,078

[22] Filed: Jun. 10, 1994

[51] Int. Cl.$^6$ .................................................. A61K 7/04
[52] U.S. Cl. ........................................ 424/61; 424/401
[58] Field of Search ............................ 424/606, 61, 401

[56] References Cited

U.S. PATENT DOCUMENTS

| | | | |
|---|---|---|---|
| 4,108,980 | 8/1978 | Duff | 424/52 |
| 4,115,307 | 9/1978 | McGilvery | 252/135 |
| 4,911,931 | 3/1990 | Baylink | 424/606 |
| 5,093,108 | 3/1992 | Pappas et al. | 424/61 |

*Primary Examiner*—Thurman K. Page
*Assistant Examiner*—Sharon Howard

[57] ABSTRACT

A non-aqueous organic composition for hardening and strengthening fingernails and toenails of human beings comprises a cosmetically acceptable organic vehicle containing a nail strengthening agent in the form of ammonium hexafluorophosphate dissolvable in this vehicle and providing an effective amount of fluoride.

4 Claims, No Drawings

NON-AQUEOUS COMPOSITION FOR HARDENING AND STRENGTHENING FINGERNAILS AND TOENAILS

BACKGROUND OF THE INVENTION

When fingernails and toenails of adults and children become weak and imbrittled, a variety of treatment can be employed to strengthen and harden such nails. Since water soluble fluorides have been used for many years to harden human teeth and since nail tissues are similar in certain respects to teeth tissue, attempts have been made to utilize water soluble flourides in treating fingernails and toenails to strengthen and harden them.

U.S. Pat. No. 4,919,920 discloses a composition for use in strengthening and hardening nails which takes the form of an aqueous vehicle having dissolved therein a keratin hardening and strengthening agent containing an effective amount of fluoride ion, the composition having a pH of 3.8 to 8. This patent further discloses a method for using this composition wherein it is formed into a cream which used to coat the surface of the nail to be treated. The coating is left in contact with the surface of the nail for at least one minute and usually for a longer period. Thereafter, the excess of the coating is removed. The method must be repeated at least once daily until the desired hardness and strength is obtained. All nail polish must be removed before treatment since the cream cannot penetrate polish. Moreover, the nail must be carefully dried after the excess cream has been removed because the polish will not otherwise adhere to the nail.

Moreover, the fluoride ion used in this composition can hydrolyze and form hydrofluoric acid which, if not washed off as instructed can etch or mottle the nail and damage the nail surface.

The present invention is directed toward both a new composition and a new method using ammonium hexafluoride phosphate in an organic vehicle which is not subject to and overcomes the disadvantages of the known composition and method discussed above.

SUMMARY OF THE INVENTION

Accordingly, it is an object of the invention to provide a new and improved composition for :use in hardening and strengthening fingernails and toe nails which employs ammonium hexafluoride phosphate dissolved in an organic vehicle.

Another object is to provide a new and improved composition of the character indicated which is in liquid form and can be incorporated into nail lacquers and nail lacquer removers to provide the desired hardening and strengthening action without altering the efficacy of these products.

Yet another object is to provide a new and improved method for using the new and improved composition wherein the composition is applied to the nail and dries almost immediately without requiring any subsequent removal.

These and other objects and advantages of this invention will either be explained or will become apparent hereinafter.

In accordance with the principles of this invention, a non-aqueous organic composition for hardening: and strengthening fingernails and toenails of human beings comprises a cosmetically acceptable organic vehicle containing a nail strengthening agent in the form of ammonium hexofluorophosphate dissolvable in said vehicle and providing an effective amount of fluoride.

The term "cosmetically acceptable" means an organic vehicle which does not discolor or attack in any manner the nail to which it is applied or cause any discomfort or inconvenience to the user. This vehicle typically is selected from the group consisting of anhydrous ethyl alcohol, anhydrous isopropl alcohol, ethyl acetate, methyl acetate, acetone, and methyl ethyl ketone.

The concentration of ammonium ammonium hexofluorophosphate in the vehicle is determined by the solubility of the chosen solvent but falls within the range from about 500 parts per million to about 10% by weight with a preferred optimum concentration within the range of about 0.5% to 2% by weight.

In order to accurately measure nail strength as well as to monitor changes in nail strength from week to week as obtained when the invention is used, special apparatus was developed for measuring the force required to bend the nail in the manner described in detail below.

EXAMPLE 1 - PREPARATION AND USE OF NAIL STRENGTHENING AND HARDENING COMPOSITION

Ammonium hexafluorophosphate is dissolved in anhydrous ethyl alcohol to produce a solution containing 0.5% by weight of hexafluorophosphate and 99.5% by weight of alcohol. This solution is applied to the nail with a swab or brush and is allowed to dry. It dries almost instantly as the alcohol evaporates. It should be applied daily until the desired hardness and strength is obtained.

In order to measure nail strength, a platform is used which positions the fingernail over a flattened cylinder. The cylinder creates a gap resulting from the curve of the nail positioned over a flat surface. Since the curve of the nail remains constant from week to week, the distance from the nail to the top of the flattened cylinder remains constant. The force required to bend the nail flat against the flattened cylinder can then be easily measured using a WAGNER force guage. The gauge indicates the force required to bend the nail in grams per square inch.

The product of Example 1 was evaluated with over two hundred subjects in groups of ten. The product was brushed onto the nail and allowed to dry. The force was measured as described above.

The results are summarized in table 1 below. Each of the ten horizontal lines records the initial force in grams and the increased force as measured over a period of up to five weeks for one typical group of each of ten separate subjects.

TABLE 1

| INITIAL | WEEK 1 | WEEK 2 | WEEK 3 | WEEK 4 | WEEK 5 |
|---|---|---|---|---|---|
| 290.5 | 211.0 | 328.0 | 418.4 | 417.0 | 507.0 |
| 182.0 | 185.5 | 230.0 | 303.3 | 304.0 | 405.0 |
| 197.0 | 255.0 | 291.0 | 397.0 | 518.5 | NA |
| 214.0 | 229.0 | 262.5 | 292.0 | NA | 444.5 |
| 248.3 | 294.5 | 236.5 | 400.5 | 448.5 | NA |
| 150.5 | 152.5 | 201.5 | NA | NA | NA |
| 147.0 | 158.3 | 221.7 | 255.0 | 289.0 | 376.0 |
| 219.0 | 235.4 | 274.5 | 290.0 | 322.5 | 469.0 |
| 212.8 | 253.0 | 284.0 | NA | NA | NA |
| 184.0 | 234.0 | NA | 387.0 | 485.5 | NA |

The initials "NA" appearing in table 1 above were inserted to explain that the particular subject did not appear at the proper date and consequently the measurement was not made.

Ammonium hexofluorophosphate in accordance with this invention can be used not only with anhydrous ethyl alcohol as described in Example 1, but can also be used with anhydrous isopropl alcohol, ethyl acetate, methyl acetate, acetone, methyl ethyl ketone, or combinations thereof as described below. Additional compositions are: ammonium hexofluorophosphate between 2.0 and 0.5 parts by weight and any one of the following vehicles in between 98.0 and 99.5 parts by weight: anhydrous isopropyl alcohol; ethyl acetate, methyl acetate, acetone, and methyl ethyl ketone.

EXAMPLE 2 - FINGERNAIL LACQUER

A nail lacquer was prepared using ingredients and methods well known in the art. The formula with the constituents expressed in parts by weight was as follows:

ethyl acetate between 19.55 and 21.05 butyl acetate 35.95 nitrocellulose ½ sec R. S. Grade 13.00 toslamide epoxy resin 9.00 dibutyl phthlate 7.50 isopropyl alcohol 2.00 anhydrous ethyl alcohol SD 3-A 5.00 camphor 3.50 parts etocrylene 0.50 parts ammonium hexafluorophosphate between 2.00 and 0.50

In this example, the acetates are solvents for ammonium hexafluorophosphate, nitrocellulose and the resin. The phthlate and camphor are plasticizing agents for nitrocellulose. Nitrocellulose is the primary film forming polymer and is the basis for any of the standard nail enamels on the market. The resin promotes adhesion and flexibility to the nitrocellulose. Eocrylene is a sun screen material which is used to prevent yellowing of the formula.

Application by brush of this lacquer to a nail established contact of the flouride with the nail for long periods of time without washing off because these coatings are very resistant to water.

EXAMPLE 3 - NAIL LACQUER REMOVER

Ammonium hexafluorophosphate is dissolved in ethyl acetate to produce a solution containing 0.5% by weight of ammonium hexafluorophosphate and 99.5% by weight of acetate.

This formula, when applied by a brush to a nail coated with a lacquer removed the nail polish while again treating the nail with hexafluorophosphate.

While this invention has been described with particular reference to detailed examples, the protection sought is to be limited only by the terms of the claims which follow.

What is claimed is:

1. A method for hardening and strengthening fingernails and toenails of human beings comprising the steps of:

providing a non-aqueous organic composition comprising a cosmetically acceptable organic vehicle containing a nail strengthening agent in the form of ammonium hexafluorophosphate dissolvable in said vehicle and providing an amount of fluoride which is sufficent to provide hardening and strenthening of nails;

applying the composition topically to the outer surface of a fingernail or toe nail; and allowing the applied composition to dry on said outer surface.

2. The method of claim 1 wherein the vehicle is a film forming nitrocellulose lacquer.

3. A method for hardening and strengthening fingernails and toenails of human beings comprising the steps of:

providing a non-aqueous organic composition comprising a cosmetically acceptable organic vehicle containing a nail strengthening agent in the form of ammonium hexafluorophosphate dissolvable in said vehicle, the ammonium hexafluorophosphate concentration falling within the range of 0.50% to 2.00% by weight;

applying the composition topically to the outer surface of a fingernail or toe nail;

allowing the applied composition to dry on said outer surface;

repeating steps and on a daily basis until the desired hardness and strength of the fingernail or toe nail is obtained.

4. The method of claim 3 including the additional step of periodically measuring the strength and hardness of the fingernail or toe nail as step is repeated to determine when the desired hardness and strength has been obtained.

* * * * *